United States Patent [19]

Jackson

[11] Patent Number: 4,517,702
[45] Date of Patent: May 21, 1985

[54] ENDOSCOPIC SCRUB DEVICE

[76] Inventor: Frank W. Jackson, Twillingate, R.D. 3, Mechanicsburg, Pa. 17055

[21] Appl. No.: 508,792

[22] Filed: Jun. 29, 1983

[51] Int. Cl.³ .............................................. B08B 9/02
[52] U.S. Cl. .................................... 15/114; 15/244 C
[58] Field of Search ........... 15/104.93, 104.94, 104.92, 15/210 B, 244 R, 244 B, 244 C, 256.6, 114, 118

[56] References Cited

U.S. PATENT DOCUMENTS

| 2,229,071 | 1/1941 | Godstrey | 15/256.6 |
| 2,255,154 | 9/1941 | Esposito | 15/244 R X |
| 3,447,181 | 6/1969 | Coker et al. | 15/104.94 |

FOREIGN PATENT DOCUMENTS 2094618  9/1982  United Kingdom ............. 15/210 B

Primary Examiner—Edward L. Roberts
Attorney, Agent, or Firm—Eugene Chovanes

[57] ABSTRACT

A self-contained cleaning device for endoscopic instruments of the type inserted into a human, or animal body through an orifice such as the rectum, wherein the cleaning device is used to quickly and efficiently clean and relatively sterilize the instrument.

3 Claims, 8 Drawing Figures

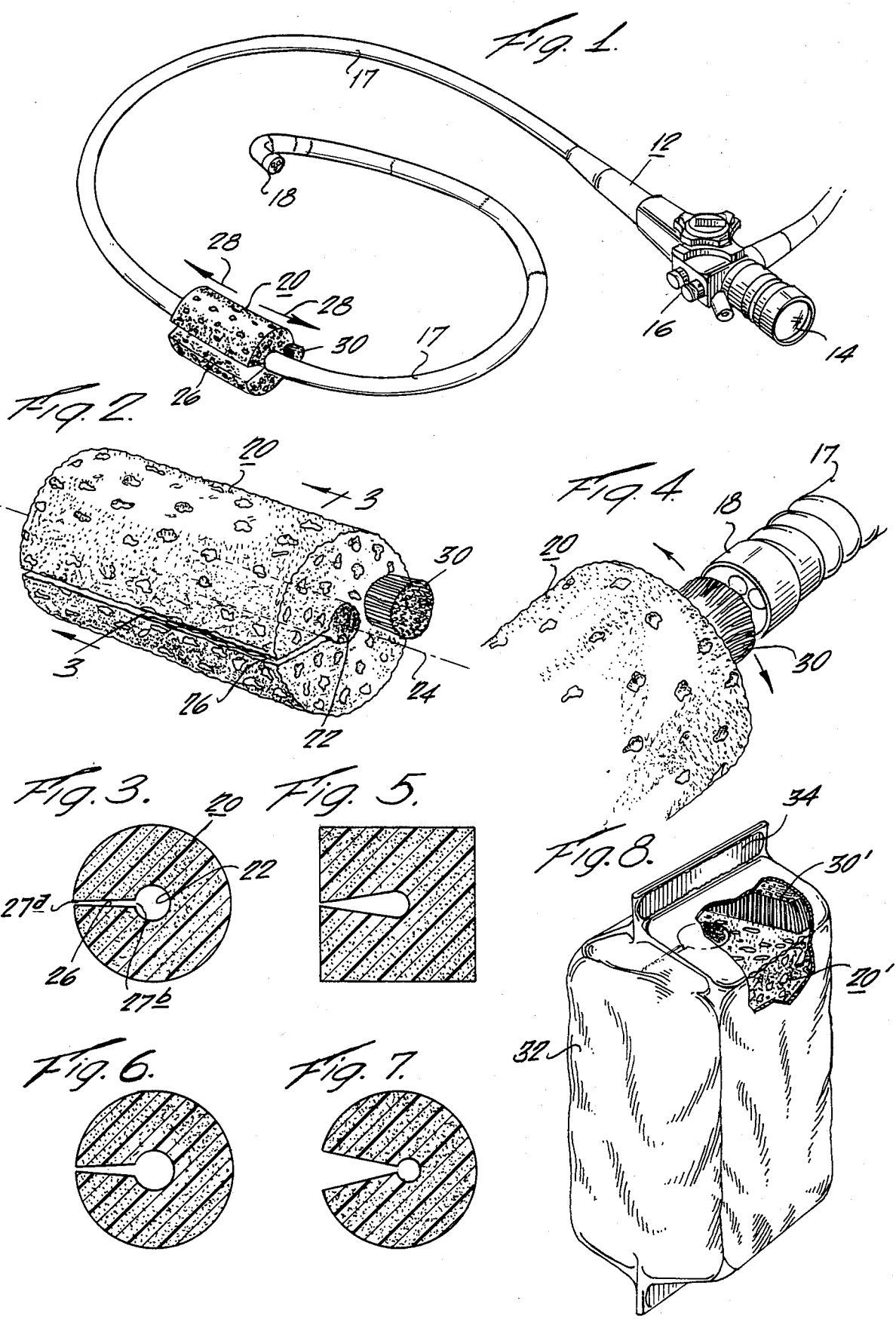

ENDOSCOPIC SCRUB DEVICE

BACKGROUND OF THE INVENTION

In the medical field, there is substantial use of what are called "endoscopic instruments" which essentially are tubelike devices which are inserted into a human body, or the body of an animal through an orifice whereby the interior of the body can be explored and in some instances operated on without the usual procedure of cutting into the body.

These instruments can be manipulated from outside the body whereby the instrument is guided into various sections internally, and observations can be made through the tubelike instrument. In some instances, auxilliary devices are used to cut, scrape, obtain biopsy specimens and the like. Encoscopes are very expensive, delicate and precise instruments, needing care in handling and cleaning to prevent damage. Moreover, as these instruments are used in internal areas of the body, extra care should be taken to prevent contamination and spread of infectious diseases such as hepatitis or typhoid, or contaminants such as salmonella.

The operator, after withdrawing the instrument from the human or animal body, must clean the instrument since the instrument generally has undesirable accumulations thereon such as feces or mucous or other body fluids or solids.

The instruments being relatively long, for instance 36" or more in length, and of a flexible, wiry construction pose a problem for cleaning in that if the device is placed under a running faucet, for instance, there is a real problem of proper maniuplation under the faucet. Also, there is a need for some type of abrasion on the surface to remove solids or fluids that adhere thereto, and it is very difficult while holding the instrument for the operator to also manipulate a cleaning instrument on the surface, such as a brush or wash rag or the like.

In other instances, a pool of water is accumulated in the sink and the instrument is immersed. Some cleaning utensil such as a scrub pad is worked over the surface.

Where there is great and constant use of many instruments, there is now a machine which has a compartment therein where the instrument is coiled and placed. A complicated sonic type of cleaning is then imparted to the instrument within the compartment. The machine is extremely expensive and requires a substantial capital investment.

As set forth above, the problems include the difficulty of efficient and proper cleaning wherein the instrument must be maniuplated and scrubbed at the same time. Additionally, there is a real danger that immersion into a body of water can harm the sensitive endoscope mechanisms and head which has very delicate fiberoptics therein.

Where a machine is used, there is a huge capital investment which is not warranted or possible where, for instance, individual practitioners work on a less busy basis than where many instruments are being used.

Quite commonly in the past, a 4×4" gauze pad has been used to clean and prepare the instrument because these pads are available and handy. Sponges, too, have been used but these materials have a strong bias to move away from the tube to be cleaned. A folded sponge is adequate to clean an endoscope tube only if the person exercises great care to ensure that the abrasiveness of the sponge surface is held against the tube and is maintained against the tube to contact the entire surface of the tube. This means often times that two hands are needed to clean the tube, plus another hand to hold the control portion. The technician faces a "no-win" choice between loss of time, damage to the equipment, and incomplete cleanliness.

A survey of over thirty hospitals reveals that currently there is a hodge-podge of cleaning processes and apparatus. Included are gauze pads and liquid soaps and detergents. These soaps and detergents have very poor bacteriacidal action.

It is known what should be done to obtain proper cleaning. The procedure should include the use of certain chemicals which should be applied to the entire device and there should be suitable abrasion or other rubbing action to apply this chemical.

Coker et al U.S. Pat. No. 3,447,181 discloses a surgical scrub device of rectangular shape, although no advantage of this shape is disclosed except that the sponge portion fits the brush portion and can be filled with detergent during manufacture. In actual use, the sponge portion releases liquid and detergent when squeezed, but unless the backing of the brush is porous (which it is not taught to be), none of this cleansing solution is directly applied to the device being scrubbed. Moreover, when the sponge portion is used in direct contact with the object to be scrubbed, the brushes must be grabbed, leading to awkward or uncomfortable problems. The same design is shown in Design Pat. No. 211,851.

While Coker et al and other designs might be of value for some purposes, they are not suitable for use by an operator who must hold the object being cleaned in one hand and thoroughly and totally contact the object with a cleaning device with the other hand.

Of course, prior art methods of placing the instrument in a bath suitably designed to prevent damage to the instrument, followed by hand scrubbing with conventional cleaning equipment including sterile surgical sponges, can be carried out. The instrument will be protected and cleaned. At the same time, valuable time in the operating room will be lost, since although time is of the essence in the operating room, sanitation and antiseptic conditions are the first order of priority. Additional expense in providing extra equipment and/or additional personnel is another cost added to the loss of time when conventional cleaning equipment is used. Use of the device away from fully equipped hospitals is also limited without improved cleaning techniques.

Accordingly, it would be of great benefit to users of endoscopic instruments, and therefore to the patients receiving the treatment, if a self-contained cleaning device could be developed which would permit safe, fast, thorough cleaning without expensive equipment and with a minimum amount of effort.

SUMMARY OF THE INVENTION

The device of the invention is a self-contained cleaning device for use in combination with endoscopic instruments having a tube portion for insertion into a body orifice. This device includes a sponge body having an axially aligned central bore sized to fit the tube portion of said instrument, with the sponge body having a slit extending parallel to and in communication with said bore to permit said body to be fitted over said tube. The slit is narrow enough so that slight gripping pressure on said body is adequate to close said slit to cause sponge body contact around the complete circumference of said tube. The body further is sized to present a radial thickness outward from said bore at least equal to the diameter of said tube. In a preferred embodiment, the sponge body is generally cylindrical in shape and the bore is centered about the axis of said cylinder. Normally the tube will have a diameter of from about 7 mm to about 12 mm. Under these conditions, the bore has a diameter of from about 5 mm to about 7 mm. The cylinder may have a radial thickness outward from the bore of from 12 to 25 mm to give an overall diameter of from 30 to 60 mm.

In another preferred embodiment, the bore is sized to have a diameter equal to or slightly less than the diameter of said tube, and said sponge body is sufficiently compressed to cause said bore to increase slightly to fit the diameter of said tube. Also, the device may be combined to include 15 to 45 cc of cleaning solution absorbed therein, such that the device and the solution are packaged in a contamination-free enclosure.

BRIEF DESCRIPTION OF THE DRAWINGS

The invention and various embodiments are readily understood from a reading of the following disclosure and the accompanying drawings, presented for illustration purposes, in which:

FIG. 1 is a perspective view showing a conventional endoscopic device about to be cleaned and scrubbed, utilizing the invention of a cleaning, sterilizing and scrubbing tool shown encircling the flexible tubelike portion of the endoscope and free to move in either direction along the flexible endoscopic device. It also should be noted in FIG. 1 that the scrubbing tool shown has just been placed in position prior to gripping and fully encircling the endoscopic tube.

FIG. 2 is a perspective view of the scrubbing tool shown in FIG. 1 in a relaxed condition prior to use.

FIG. 3 is a transverse sectional view taken on the line 3—3 of FIG. 2, showing additional details of the device.

FIG. 4 is a perspective view illustrating the use of the soft brushlike scrubbing attachment shown on one terminal face of the device as shown in FIG. 2.

FIGS. 5 through 7 show various cross-sectional modifications of the device shown in prior figures.

FIG. 8 is a perspective view illustrating a modified form of the invention including a packaging item of the scrubbing device of the invention and, in this instance, the scrubbing tool shown in full within the package is a modified form having a cross-sectional shape such as shown in FIG. 5.

DETAILED DESCRIPTION OF THE INVENTION

An endoscope 12 of conventional design is shown generally in FIG. 1 with a viewer 14 and control unit 16. Tube 17 is intended to be inserted into a body orifice, so that the distal end 18 can perform its function. A sponge body 20 has, in FIG. 1, just been placed in position on tube 17 prior to gripping and fully encircling the endoscopic tube 17. The sponge body 20 is designed so that gripping it with very little pressure will be adequate to cause the sponge body 20 to be in contact with the complete circumference of tube 17.

In FIG. 2, the body 20 is shown in a relaxed position prior to use with tube 17. Central bore 22 is positioned along axis 24 of body 20. A slit 26 is cut in body 20, and is parallel with bore 22. This permits the tube 17 to be passed through slit 26 to fit inside bore 22. Movement of body 20, as shown by arrows 28, as shown in FIG. 1, permits the tube 17 to be scrubbed in such a way that one hand is needed to close and maneuver the sponge body 20 to cause abrasion by the sponge on the entire tube. Body 20 may also be fitted with brush 30 as an added feature, so that brush 30 may cleanse distal end 18 of tube 17, as shown in FIG. 4. Brush 30 may be sized to fit common sizes of distal ends, and its combination with body 20 provides a single-tool completeness, making rapid work possible.

The shape of slit 26 may vary, as shown in FIG. 5, FIG. 6 and FIG. 7, depending upon the various methods which might be used to install or cut the slit 26 in the body 20. Slits 26 are preferably to those in FIG. 3 which have a cut or gap 27a which is narrower at the outside of the cylindrical body 20 than the cut or gap 27b at the bore 22 of the body 20. This taper from cylinder surface to bore acts to bias the body 20 on to tube 17 in such a manner that slight pressure causes total contact of all of the circumference of tube 17. Even in FIG. 7, where the slit 26 is tapered in the opposite way, the gap 27b is smaller than bore 22. Once the bore 22 surrounds tube 17, again slight pressure is all that is needed to cover the surface of tube 17.

All of the body portions 20 shown in these drawings have sufficient thickness so that the distance radially outward from 27b to 27a is at least equal to the diameter of the tube 17. This means that the body 20 will have a diameter which is twice the distance from 27a to 27b plus the diameter of tube 17. As has been indicated above, the typical endoscope tube 17 has a diameter of from about 7 mm to about 12 mm. The bore 22 will have a diameter to accommodate the tube, preferably from about 5 mm to 7 mm, keeping in mind the compressible nature of body 20. The bore can readily be increased by compression of the sponge so that it fits the diameter of tube 17. It is preferred that the radial thickness or distance between 27a and 27b will be from about 12 to more than 25 mm. The body 20 will have an overall diameter of from 30 to more than 60 mm.

As was shown above, the addition of a brush 30 permits the use of a single device to clean all of the tube 17 and distal end 18. In another embodiment, the body 20 may be filled with a cleaning solution, such as an appropriate soap or detergent, disinfectant, hexachlorophene or the like. The body, with or without added fluid, could be packaged in a disposable package such as that shown in FIG. 8. The body 20' and brush 30' in package 32 is a self-contained unit, readily accessible via seal 34 to permit use with an endoscope. The device of this invention, in the prepackaged and disposable form, would elevate and would make more uniform cleaning practices, and would eliminate prior problems experienced when an ordinary sponge is used repetitively.

As shown in FIG. 1, in use the sponge 20 is simply slid over the tube 17 through the slit 26, and then it is worked along the tube the entire length back and forth, with a grating action. The hand grasping the sponge can exert whatever pressure and whatever grip is found to be desirable, since only slight pressure is needed to close the slit.

In use, there is a pool of clear water formed in the sink, then as the sponge is worked along the tube, the soapy solution disperses into the water. Meanwhile, suction can be applied at the working end via control unit 16. This is done sequentially after the scrubbing action is completed externally and the sponge yields its soapy solution into the water. Next, the suction is applied at the head end in the same manner as when the endoscope is used. This results in drawing the soapy solution (which has just been formed by the sponge) through the interior of the endoscope and provides for further cleaning of both the exterior and the interior.

Having thus described the invention, what is claimed is:

1. A self-contained cleaning device for use in combination with endoscopic instruments having a tube portion for insertion into a body orifice, comprising: a generally cylindrical shaped sponge body having an axially aligned central bore sized to fit the tube portion of said instrument, said sponge body having a slit extending parallel to and in communication with said bore to permit said body to be fitted over said tube, said slit being narrow enough so that slight gripping pressure on said body is adequate to close said slit to cause sponge body contact with the complete circumference of said tube, said body further being sized to present a radial thickness outward from said bore at least equal to the diameter of said tube, and a brush extending outwardly from an end of said sponge body adapted to clean instrument portions.

2. The device of claim 1, wherein said tube has a diameter of from about 7 mm to about 12 mm, and said bore has a diameter of from about 5 mm to about 7 mm.

3. The device of claim 1 wherein said bore is sized to have a diameter equal to or slightly less than the diameter of said tube, and said sponge body is sufficiently compressible to cause said bore to increase slightly to fit the diameter of said tube.

* * * * *